(12) United States Patent
Zhilov et al.

(10) Patent No.: US 7,776,833 B2
(45) Date of Patent: Aug. 17, 2010

(54) USE OF CYCLIC BIOISOSTERS OF PURINE SYSTEM DERIVATIVES FOR TREATING DISEASES PRODUCED BY DISORDERS OF NITERERGIC AND DOPAMINERGIC SYSTEMS

(75) Inventors: Valery Khazhmuratovich Zhilov, Ul. Ploshchad Pobed, d. 1, korp. B, Kv. 49, Moscow (RU) 121170; Sergei Vladimirovich Zhuravlev, Moscow (RU); Alexander Nikolaevich Markov, Moscow (RU); Vladimir Mikhailovich Polosin, Moscow (RU)

(73) Assignee: Valery Khazhmuratovich Zhilov, Moscow (RU)

( * ) Notice: Subject to any disclaimer, the term of this patent is extended or adjusted under 35 U.S.C. 154(b) by 400 days.

(21) Appl. No.: 10/567,113

(22) PCT Filed: Aug. 3, 2004

(86) PCT No.: PCT/RU2004/000298

§ 371 (c)(1),
(2), (4) Date: Feb. 3, 2006

(87) PCT Pub. No.: WO2005/011648

PCT Pub. Date: Feb. 10, 2005

(65) Prior Publication Data

US 2007/0135636 A1 Jun. 14, 2007

(30) Foreign Application Priority Data

Aug. 4, 2003 (WO) .................... PCT/RU03/00346

(51) Int. Cl.
*A01N 43/04* (2006.01)
*A61K 31/70* (2006.01)

(52) U.S. Cl. ..................... 514/43; 514/42; 514/183; 514/184; 514/185; 514/186

(58) Field of Classification Search ........................ None
See application file for complete search history.

(56) References Cited

U.S. PATENT DOCUMENTS

| 4,547,507 A | 10/1985 | Clements-Jewery |
| 4,600,714 A | 7/1986 | Gaitanopoulos et al. |
| 4,612,316 A | 9/1986 | Andersson et al. |
| 4,650,805 A | 3/1987 | Jaen et al. |
| 4,727,079 A | 2/1988 | Bodor |
| 4,904,676 A | 2/1990 | Rae et al. |
| 5,196,432 A | 3/1993 | Crichlow |
| 5,256,660 A | 10/1993 | Swan |
| 5,281,594 A | 1/1994 | Piercey et al. |
| 5,476,855 A * | 12/1995 | el Kouni et al. ............. 514/269 |
| 5,597,820 A | 1/1997 | Hori et al. |
| 5,719,151 A | 2/1998 | Shall et al. |
| 5,723,496 A | 3/1998 | Nakada |
| 5,753,706 A | 5/1998 | Hsu |
| 5,883,094 A | 3/1999 | Sanner et al. |
| 5,889,010 A | 3/1999 | Sanner et al. |
| 6,521,623 B1 | 2/2003 | Monferini et al. |

FOREIGN PATENT DOCUMENTS

| EP | 0617024 A1 | 2/1994 |
| EP | 0 612 733 A | 8/1994 |
| EP | 0612733 A1 | 8/1994 |

(Continued)

OTHER PUBLICATIONS

Goldberg Clinical Therapeutics (1998), vol. 20, pp. 1033-1048.*

(Continued)

*Primary Examiner*—Patrick T Lewis
(74) *Attorney, Agent, or Firm*—Locke Lord Bissell & Liddell LLP

(57) ABSTRACT

The invention relates to application of compounds having a general structural formula:

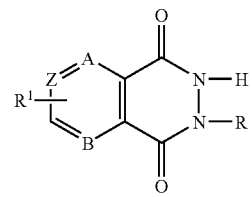

where R=

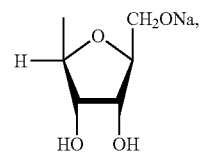

Li, Na, K,
$R^1$=—H, —$NH_2$, —Br, —Cl, —OH, —COOH,
B=—N=, —CH=, Z=—CH=, —N=,
A=—N= at B=—N=, Z=—CH—,
A=—CH= at B=—N=, Z=—CH—,
A=—CH= at B=—N=, Z=—N=,
A=—CH= at B=—CH=, Z=—CH=,
A=—CH= at B=—CH=, Z=—N=,
and/or their pharmacologically acceptable salts as an active ingredient having appropriate activity with respect to nitergic and/or dopaminergic systems, in a pharmaceutical composition as neuroprotector for improvement of the cognitive function and for normalization of psychophysiological status, as well as for treatment of a wide spectrum of psychological diseases, cardiovascular diseases, diseases caused by substance abuse, and diseases caused by a hyperactive immune system in mammals including human beings.

10 Claims, 4 Drawing Sheets

FOREIGN PATENT DOCUMENTS

| | | | |
|---|---|---|---|
| EP | 0 617 024 | A | 9/1994 |
| EP | 1 203 587 | A | 5/2002 |
| EP | 1203587 | A1 | 5/2002 |
| JP | 50 046697 | A | 4/1975 |
| JP | 50046697 | | 4/1975 |
| JP | 05-078356 | | 3/1993 |
| RU | 2014077 | C1 | 6/1994 |
| RU | 2 168 511 | | 8/1998 |
| RU | 2 163 122 | | 2/2001 |
| RU | 2 169 139 | C | 6/2001 |
| RU | 2169139 | | 6/2001 |
| RU | 2 185 173 | | 7/2002 |
| RU | 2 211 036 | | 8/2003 |
| WO | 02/09681 | A | 2/2002 |
| WO | WO 02/09681 | A2 | 2/2002 |

OTHER PUBLICATIONS

Trump B.F, Berezesky I.K. "The role of altered [$Ca^{2+}$] in regulation in apoptosis, oncosis and necrosis". Biochem. Biophys. Acta, 1996, v. 1313, p. 173-178.

Roos A., Boron W.F. "Intracellular pH". Physiol. Rev., 1981, v. 61, p. 296-434.

Akotov V.S., Grobova M.E., Rkshevoi Yu.V. "Intracellular pH and substrate depenedence of proliferation of fibroblasts of Chinese Hamster". Cytology, 1991, 33(7), p. 86-94.

Gillies R.G., Martinez-Zaguilan R., Peterson E.P., Perona R. "The role of intracellular pH in mammalian cell proliferation". Cell. Physiol. Biochem., 1992, 2, p. 159-179.

Akatov V.S., Grobova M.E. "Activation of intracellular pH regulating systems upon cell adhesion to solid substrate". Biol. Membr., 1993, v.6, p. 917-934.

Kapus A., Romanek R., Qu A.Y.Rotstein O.O., Grinstein S.A. "pH-sensitive and voltage-dependent proton conductance in the plasma membrane of macrofages". J. Gen. Physiol., 1993, vol. 02 (4), p. 723-760.

Demaurex N., Downey G., Waddell T., Grinstein S. "Intracellular pH regulator during spreading of human neutrophils", J.Cell. Biol., 1996, v. 133, p. 1381-1402.

Tannock I.A., Rotin D. "Acid pH in tumors and its potential for therapeutic exploration". Cancer Res., 1989, v.49, p. 4373-4384.

Stabbs M., Rodrigues L., Howl F.A., Wang I., Joeng K.S., Veech R.L., Griffiths J.R. "Metabolic consequences of a reversed pH gradient in rat tumors". Cancer Res., 1994, v.54, p. 4011-4016.

Mashkovsky M.D., "Medicinal Agents". Moscow, Medicine, 1993, part II, p. 137-140.

Taguchi Hiroshi. "A new fluorometric assay method for guinolinic acid". Analitic Biochemistry, 1983, 131 (1), p. 194-197.

Huntress E.H., Stanley L.N., Parker A.S. "The preparation of 3-Aminophtalhydrazide for use in the Demonstration of Chemiluminescence", J, Am. Chem. Soc., 1994, v. 56, p. 241-242.

Zyczynska—Baloniak I., Czajka R., Zinkowska E., Synthesis of Derivatives of 4-Hydroxypyrazine-[2,3-d]pyridazine-I-one. Polish Journal of Chemistry. 1978, v. 52, p. 2461-2465.

Kormendy K., Ruff F. "Pyridazines condensed with a Heterering. III"., Acta Chimika Hungarika. 1990, 127 (2), p. 253-262.

Yurugi S., Hieda M. "Studies on the synthesis of N- Heterocyclic Compounds". Chemistry, Pharmaceutic Bull., 1972, v. 20 (7), p. 1522-1527. ibid., p. 1513-1521.

Seo E., Kuwana T. "Polarography of cyclic Hydrazides", J. Electroanal. Chem., 1963, v. 6, p. 417-418.

Lund H. "Polarographic and electropreparative reduction of 1(2H)-phthalazines, 2,3-dihydro-I,4 phthalazindiones and related compounds", Coll. Czechoslow. Chem.Com., 1965, v. 30. p. 4237-4249.

Ganz M.B. et all. "Argininvasopression enchangers of pH, regulation in the presence of HCO__ by stimulating three acid-base transport systems", Nature, 1989, v. 337, p. 648-651.

Rogachev B., Hausmann M.J., Julzari R., Weiler H., Holmes C., Falct D., Chaimovitz C., Douvdevani A. Effect of bicarbonat-based dialysis solution on intracellular pH (pH,) and TNF-alpha production by peritoneal macrophages, Perit. Dial. Int., Nov.-Dec. 17, 1997(6), p. 543-553.

Bidani A., Heming T.A. "Effect of concanavalin A on $Na^+$-dependent and $Na^+$-independent mechanism for $H^+$ extrusion in alveolar macrophages", Lung., 1998, 176 (1), p. 25-31.

Swallow C.J., Grinstein S., Sudsbury R.A., Rotstein O.D. "Relative roles of $Na^+/H^+$ exchange and vacuolar-type $H^+$ ATPases in regulating cytoplasmic pH and Function in murine peritoneal macrophages", J. Cell. Physiol., 1993, 157 (3), p. 453-460.

Koshevoi Yu.V., Akatov V.S., Grobova M.E., "Microspectrofluorimeter for measuring endocellular pH (micro pH)". Devices and equipment for studies in the field of physical-and-chemical biology and biotechnology. Pushchino, 1990. p. 8-14.

Thomas J.A., Bushbaum R.N., Zimniak A.w Racker E. "Intracellular pH measurements in Ehrlich ascites tumor cells utilizing spectroscopic probe generated in situ", Biochemistry, 1979, v. 18, p. 2210-2218.

Li J., Eastman A. "Apoptosis in an interleukin-2-depended cytotoxic T-lymphocyte cell line is associated with intracellular acidification", J.Biol. Chem., 1995, v. 270. , No. 7, p. 3203-3211.

Solovieva M.E., Akatov V.S., Leshchenko V.V., Kudryavtsev V.A. "The mechanism of destruction of cells of myeloma NS/O in culture". Proceeding of the Russian Academy of Sciences, 1998, 2, p. 194-189.

Zhu W.-H., Loh T.-T. "Effects of Na+/H+ antiport and intracellular pH in the regulation of HL-60 cell apoptosis", Biochim. Biophys. Acta, 1995, v. 1269, p. 122-128.

Brenton P.D. "Mechanistic Aspect of Diazaquinone Chemiluminescence", Aust. J. Chem., 1984, v. 37, p. 1001-1008.

Nishikimi M. Rao N.A. and Yagi K. "The occurrence of superoxide anion in the reaction of reduced phenasine methosulfate and molecular oxygen". Biochem. Biophys. Res. Commun., 1972, v. 46, p. 849-855.

Rahman S., Ali Khan R., Kumar A. "Experimental study of the morphine deaddiction properties of Delphinium denudatum Wall/ BMC Complement Altem". Med. 2002, v. 29, p. 1-6.

Dum J., Blasig J., Herz A. Buprenorphine: "Demonstration of physical dependence liability". Eur. J. Pharmacol., 1981, v. 70. p. 293-300.

Misko T.R., Schilling R.J., Salvemini D. et al. "A fluorometric assay for the measurement of nitrite of biological samples". Anal. Biochem., 1993, v. 214, p. 11-16.

Bredt and Snyder. "Nitric oxide mediates glutamate-linked enhancement of cGMP levels in the cerebellum". Proc. Natl. Acad. Sci. USA, 1989, v. 86, p. 9030-9033.

Kiss J.P., Vizi E.S., "Nitric oxide: a novel link between synaptic and nonsynaptic transmission," Trends Neurosci., Apr. 2001, 24 (4):211-5.

Paul I.A., Skolnick P., "Glutamate and depression: clinical and preclinical studies," Ann. N Y Acad. Sci., Nov. 2003; 1003:250-72.

Girgin Sagin F., Sozmen E.Y., Ersoz B., Mentes G., "Link between monoamine oxidase and nitric oxide," Neurotoxicology, Jan. 2004, 25 (1-2): 91-9.

Vizi E.S. "Role of high-affinity receptors and membrane transporters in nonsynaptic communication and drug action in the central nervous system," Pharmacol. Rev., Mar. 2000, 52 (1): 63-89.

Liu Y., "Nitric oxide effect dopaminergic processes", Adv. Neuroimmunol., 1996, 6 (3): 259-64.

Chiavegatto S., Nelson R.J., "Interaction of nitric oxide and serotonin in aggressive behavior," Horm. Behav., Sep. 2003, 44 (3): 233-41.

Pfaus J.G., "Neurobiology of sexual behavior", Curr. Opin. Neurobiol., Dec. 1999, 9 (6): 751-8.

Stefano G.B., "Autoimmunovascular regulation: morphine and anandamide and ancondamide stimulated nitric oxide release", J.Neuroimmunol., Mar. 1998, 15, 83 (1-2): 70-6.

Tayfun Uzbay I., "Oglesby M.W. Nitric oxide and substance dependence," Neurosci. Biobehav. Rev., Jan. 2001, 25 (1): 43-52.

Kiss J.P. "Role of nitric oxide in the regulation of monoaminergic neurotransmission", Brain Res. Bull., Aug. 2000, 52 (6): 459-66.

Mandel S., Grunblatt E., Riederer P., Gerlach M., Levites Y., "Youdim M.B. Neuroprotective strategies in Parkinson's disease: an update on progress", CNS Drugs, 2003, 17 (10): 729-62.

Ujike H., "Advanced findings on the molecular mechanisms for behavioral sensitization to psychostimulants", Nippon Yakurigaku Zasshi., Jan. 2001, 117 (1): 5-12.

Olesen J., Jansen-OlesenI., "Nitric oxide mechanisms in migraine." Pathol. Biol., Paris, Sep. 2000, 48 (7): 648-57.

Missale C., Nash S.R., Robinson S.W., Jaber M., Caron M.G., "Dopamine receptors: from structure to function", Physiol. Rev., Jan. 1998, 78 (1): 189-225.

Zawilska J.B. "Dopamine receptors-structure, characterization and function", Postepy, Hig. Med. Dosw., 2003, 57 (3): 293-322.

Fagen Z.M., Mansvelder H.D., Keath J.R., Mc. Gehee D.S., "Short- and long-term modulation of synaptic inputs to brain reward areas by nicotine", Ann., NY Acad. Sci., Nov. 2003, 1003: 185-95.

Ujike H., "Molecular biology of drug dependence and behavioral sensitization", Seishin Shinkeigaku Zasshi., 2002, 104 (11): 1055-68.

Wolf M.E., Mangiavacchi S., Sun X., "Mechanisms by which dopamine receptors may effect synaptic plasticity", Ann. NY Acad. Sci., Nov. 2003, 1003: 241-9.

Kosten T.R., George T.P., Kosten T.A., "The potential of dopamine agonists in drug addiction", Expert Opin. Investig. Drugs, Apr. 2002,11 (4): 491-9.

Pearlson G.D. "Neurobiology of schizophrenia", Ann. Neurol., Oct. 2000, 48 (4):556-66.

Abi-Dargham A., Moore H. , "Prefrontal DA transmission at D1 receptors and the pathology of schizophrenia", Neuroscientist, Oct. 2003, 9 (5): 404-16).

Conley R.R., Kelly D.L. "Current status of antipsychotic treatment" Curr. Drug Target CNS. Neurol. Disord., Apr. 2002, 1 (2): 123-8.

Taylor D.P., Riblet L.A., Stanton H.C., Eison a.S., Eison A.S., Temple DL Jr.. "Dopamine and antianxiety activity", Pharmacol. Biochem. Behay., 1982, 17, Suppl. 1: 25-35.

Kapur S., Mamo D. "Half a century of antipsychotics and still a central role for dopamine D2 receptors", Prog. Neuropsychopharmacol. Biol. Psychiatry, Oct. 2003, 27 (7): 1081-90.

Taguchi Hiroshi. "A new fluorometric assay method for quinolinic acid". Analitic Biochemistry, 1983, 131 (1), p. 194-197.

Dum J, Blasig J, Herz A, "Buprenorphine: demonstration of physical dependence liability", Eur. J. Pharmacol., 1981, V. 70, p. 293-300.

Rahman S., Ali Khan R., Kumar A., "Experimental study of the morphine de-addiction properties of Delphinium denudatum Wall", BMC Complement Altern. Med., 2002, V.29, p. 1-6.

Blasig J., Herz A., Reinhold K., Zieglgansberger S. "Development of physical dependence on morphine in respect to time and dosage and quantification of the precipitated withdrawal syndrome in rats"Psychopharmacologia, Berlin, 1973, V.33, p. 19-38.

Rahman S., Ali Khan R., Kumar A. "Experimental study of the morphine de-addiction properties of Delphinium denudatum" Wall, BMC Complement Altern. Med., 2002, V.29, p. 1-6.

Lei B., Adachi N., Nagaro T., Arai T. "Measurement of total nitric oxide metabolite (NO (x) (−)) levels in vivo. Brain", Res. Protoc., 1999, V. 4, p. 415-419.

Bredt M., Snyder S. "Nitric oxide mediates glutamate-linked enhancement of cGMP levels in the cerebellum", Proc. Natl. Acad. Sci., USA, 1989, V.86, p. 9030-9033.

Bradford M. M. "A rapid and sensitive method for quantitation of microgram quantities of protein using the principle of protein binding" Anal. Biochem., 1976, V. 72, p. 248-254.

Giuliano F., Allard J. "Dopamine and male sexual function" Eur. Urol., 2001, 40 (6), 601-608.

Iuliano F., Allard J., Rampin O. et. al. "Pro-erectile effect of systemic apomorphine: existence of a spinal site action" J. Urol., 2002, 167 (1), 402-406.

Brien S.E., Smallegange C., Gofton W.T., et.al. "Development of a rat model of sexual performance anxiety: effect of behavioral and pharmacological hyperadrenergic stimulation on apomorphine-induced erections" Int. J. Impot. Res., 2002, 14 (2), 107-115.

* cited by examiner

USE OF CYCLIC BIOISOSTERS OF PURINE SYSTEM DERIVATIVES FOR TREATING DISEASES PRODUCED BY DISORDERS OF NITERERGIC AND DOPAMINERGIC SYSTEMS

This is a US national phase application under 35 U.S.C. §371 of international application PCT/RU2004/000298, filed Aug. 3, 2004, hereby incorporated by reference in its entirety, which is a continuing application of, and claims benefit under 35 U.S.C. §120 to, co-pending international application PCT/RU2003/000246, filed Aug. 4, 2003, which designated the United States of America and of which is hereby incorporated by reference in its entirety.

FIELD OF INVENTION

The invention relates to medicine, in particular, to pharmaceutical compositions having a directed action to important mediator systems of an organism, in particular, for treatment of various diseases associated with nitrergic and dopaminergic systems of an organism. Such diseases include neurologic, neuropsychic and cardiovascular diseases.

PRIOR ART

It is well known that a number of diseases of the nervous system and cardiovascular diseases, in particular, substance abuse (narcotics, alcohol, nicotine and other substances), and various mental disorders associated with disturbances in functioning of neurotransmitter systems. The state of these important systems determines a psychophysiological status of a human being and practically all functions of the central and peripheric nervous system in a norm and at pathology. These systems, in particular, include nitrergic and dopaminergic systems.

Nitric oxide (from hereon referred to as NO) is low-molecular gas of free-radical nature and it easily penetrates through cellular membranes and components of an intercellular matrix, thus playing an important role in the various physiological processes. The influence of NO on the cell state significantly depends on the amount of this gas. In a low amount produced mainly by the neuronal and endothelial isoforms of NO-synthase, the NO effects are mainly associated with the effect on the heme group of the soluble form of the enzyme guanylate cyclase. The activated enzyme synthesizes cyclic guanosine monophosphate (cGMP), which controls the activity of the membrane ion channels, processes of protein phosphorylation, activity of phosphodiesterase and other reactions. In high concentrations produced by the macrophage isoform of NO-synthase, NO can render a toxic effect on cells associated both with direct action on Fe-containing enzymes and with formation of a strong oxidizer-free-radical compound peroxynitrite ($ONOO^-$), which is form is realized first of all in an inhibition of mitochondrial enzymes resulting in a decrease of adenosine triphosphate production of (ATP), as well as in production of enzymes participating in DNA replication. The capability of peroxynitrite and NO to damage DNA results in an activation of protective mechanisms, in particular, in an activation of the enzyme of poly (ADP-ribose) synthase that, in turn, results in a decrease of the ATP level and can lead to a destruction of the cell.

NO is synthesized in a cell from L-arginine by the enzyme NO-synthase (from hereon referred to as NOS) converting L-arginine into NO and citrulline. This synthetic process is realized, in particular, in the cardiovascular system and central nervous system (from hereon referred to as CNS), where NO performs a function of a signal molecule with a neurotransmitter function. The neurotransmitter function of NO is confirmed by its synthesis at neuronal excitation, diffusion into neighbor cells, where it activates generation of cGMP capable of affecting the conductivity of ionic channels, and, thus, changing neuronal electrogenesis. Together with this, the NO performs a new (not synaptic and not mediated by receptors) type of the interneuronal communications in the CNS (Kiss J. P., Vizi E. S. Nitric oxide: a novel link between synaptic and nonsynaptic transmission. Trends Neurosci., 2001, Apr., 24 (4):211-5).

The effect of the nitrergic system on the CNS function is carried out both directly and indirectly through other neuromediator systems. For example, glutamate and its receptors mediate the major functions of the CNS, including memory, and also affect the development of depression and antidepressant activity. NO and NOS are important components of the system signal transduction of in the glutamergic synapse (Paul I. A., Skolnick P. Glutamate and depression: clinical and preclinical studies. Ann. N Y Acad. Sci., 2003, November; 1003:250-72). It has been shown that the activity of monoamine oxidase, a key enzyme of monoamine metabolism in the brain is associated with the amount of NO in a cell (Girgin Sagin F., Sozmen E. Y., Ersoz B., Mentes G. Link between monoamine oxidase and nitric oxide. Neurotoxicology, 2004, January, 25 (1-2): 91-9).

NO affects the function of monoaminergic transporters (Vizi E. S. Role of high-affinity receptors and membrane transporters in nonsynaptic communication and drug action in the central nervous system. Pharmacol. Rev., 2000, March, 52 (1): 63-89). NO facilitates release of human monoamines, particularly dopamine, and, if necessary, blocks the presynaptic reuptake of dopamine. Therefore, NO increases lifetime of dopamine in the synapse. Due to participation of dopamine in locomotor and psychological processes, the nitrergic effects on these processes attract increasing attention of specialists (Liu Y. Nitric oxide effect dopaminergic processes. Adv. Neuroimmunol., 1996, 6 (3): 259-64).

NO mediates behavioral and neuroendocrine reactions of a human organism, in particular, aggressive and impulsive behavior. NO plays an important role in functioning of serotonin receptors of the brain (Chiavegatto S., Nelson R. J. Interaction of nitric oxide and serotonin in aggressive behavior. Horm. Behav., 2003, September, 44 (3): 233-41). The monoaminergic systems and the NO system of hypothalamus, limbic and stem structures take part in regulation of sexual behavior, control partner preference, sex desire, erection, copulation, ejaculation, orgasm and sexual satisfaction) (Pfaus J. G. Neurobiology of sexual behavior. Curr. Opin. Neurobiol., 1999, December, 9 (6): 751-8).

It is well known that NO plays an important role in forming of dependence on various drugs, including opioids, ethanol, psychostimulants and nicotine. In particular, NO takes part in manifestation and development of abstinence symptoms. For example, activation of opiate receptor µ3 is accompanied by NO release in the endothelial cells, granulocytes, monocytes and microglia (Stefano G. B. Autoimmunovascular regulation: morphine and anandamide and ancondamide stimulated nitric oxide release. J. Neuroimmunol., 1998, March, 15, 83 (1-2): 70-6). NO plays an important role in development of dependence from various classes of drugs of abuse. Thus, the modulation of the NO system can be a potential therapeutic target for treatment of various substance dependences (Tayfun Uzbay I., Oglesby M. W. Nitric oxide and substance dependence. Neurosci. Biobehav. Rev., 2001, January, 25 (1): 43-52).

NO participates in regulation of neurotransmission in the CNS, in particular, mediating nonsynaptic interaction, controlling the monoaminergic systems such as dopaminergic and noradrenergic systems. Thus, the dysfunction of the NO system is directly connected with the main neuropsychic diseases, for example, depression, Parkinson's disease and others (Kiss J. P. Role of nitric oxide in the regulation of monoaminergic neurotransmission. Brain Res. Bull., 2000, August, 52 (6): 459-66).

An increased level of monoamine oxidase, oxidative stress, excitotoxicity and excessive synthesis of NO are typical for neurodegenerative diseases, such as Alzheimer's disease and Parkinson's disease, stroke , etc. (Mandel S., Grunblatt E., Riederer P., Gerlach M., Levites Y., Youdim M. B. Neuroprotective strategies in Parkinson's disease: an update on progress. CNS Drugs, 2003, 17 (10): 729-62).

The development of dependencies and psychoses is based on behavioral sensitization, mediated by dopamine receptors D1, as well as NMDA receptors with a subsequent increase of NOS activity (Ujike H. Advanced findings on the molecular mechanisms for behavioral sensitization to psychostimulants. Nippon Yakurigaku Zasshi., 2001, January, 117 (1): 5-12).

An excessive release of NO from blood vessels, perivascular endings of nerves or from brain is considered a molecular mechanism starting spontaneous pains in migraine (Olesen J., Jansen-Olesen I. Nitric oxide mechanisms in migraine. Pathol. Biol., Paris, 2000, September, 48 (7): 648-57).

Dopamine (from hereon referred to as DA) is a major neurotransmitter and neuromodulator which plays an important role in the organism. In the CNS DA participates in the control of movement, cognitive functions, emotionality, neuroendocrine secretion and function of retinal cells. At the periphery DA participates in regulation of a homeostasis, vascular tone, and hormonal secretion. In the CNS DA receptors are represented in different brain areas (Missale C., Nash S. R., Robinson S. W., Jaber M., Caron M. G. Dopamine receptors: from structure to function. Physiol. Rev., 1998, January, 78 (1): 189-225). Various physiological functions of DA are mediated by at least five families of DA receptors: D1-D5. The dysfunction of these receptors is observed in various disorders and diseases of the CNS, in particular, in Parkinson's disease (Zawilska J. B. Dopamine receptorsstructure, characterization and function. Postepy, Hig. Med. Dosw., 2003, 57 (3): 293-322).

The dopamine signaling in certain areas of brain is a key element in the development of drug abuse (Fagen Z. M., Mansvelder H. D., Keath J. R., Mc. Gehee D. S. Short- and long-term modulation of synaptic inputs to brain reward areas by nicotine. Ann., NY Acad. Sci., 2003, November, 1003: 185-95). The interaction with the DA receptors underlies acute effects of amphetamine and cocaine (Ujike H. Molecular biology of drug dependence and behavioral sensitization. Seishin Shinkeigaku Zasshi., 2002, 104 (11): 1055-68; Wolf M. E., Mangiavacchi S., Sun X. Mechanisms by which dopamine receptors may effect synaptic plasticity. Ann. NY Acad. Sci., 2003, November, 1003: 241-9). DA agonists mediate dependence on alcohol, nicotine and stimulators (Kosten T. R., George T. P., Kosten T. A. The potential of dopamine agonists in drug addiction. Expert Opin. Investig. Drugs, 2002, April, 11 (4): 491-9).

It is hypothesized that the disorders of the dopaminergic system form a basis of schizophrenia (Pearlson G. D. Neurobiology of schizophrenia. Ann. Neurol., 2000, October, 48 (4): 556-66). The dopamine hypothesis of schizophrenia postulates a disbalance of the cortical/subcortical DA system and disturbances in functioning of DA receptors D1 (Abi-Dargham A., Moore H. Prefrontal DA transmission at D1 receptors and the pathology of schizophrenia. Neuroscientist, 2003, October, 9 (5): 404-16). Together with schizophrenia, the etiology of other psychotic diseases is associated with disturbances in the regulation of brain dopamine system (Conley R. R., Kelly D. L. Current status of antipsychotic treatment. Curr. Drug Target CNS. Neurol. Disord., 2002, April, 1 (2): 123-8.).

The dopamine mechanisms mediate etiology and symptoms of anxiety (Taylor D. P., Riblet L. A., Stanton H. C., Eison A. S., Eison M. S., Temple D L Jr. Dopamine and antianxiety activity. Pharmacol. Biochem. Behav., 1982, 17, Suppl. 1: 25-35), and many drugs with antipsychotic action modulate activity dopamine of receptors D2 (Kapur S., Mamo D. Half a century of antipsychotics and still a central role for dopamine D2 receptors. Prog. Neuropsychopharmacol. Biol. Psychiatry, 2003, October, 27 (7): 1081-90).

Thus, in the development of human pathologies disturbances of the nitrergic system are directly associated with disturbances of the dopaminergic system. These pathologies include chemical dependencies—disorders caused by misusing substances, such as dependence on narcotics, alcohol and nicotine, sleep disorders, sexual disorders, including sexual dysfunction, gastro-intestinal disorders, psychoses, affective disorders, non-organic psychoses, disorders of personality, psychiatric mood disorders, schizophrenia and schizoaffective disorders, polydipsia, bipolar disorders, dysphoric mania, anxiety and the associated diseases, obesity, bacterial infections of the central nervous system, such as meningitis, learning disorders, memory disorders, Parkinson's disease, depression, extrapyramidal side effects of neuroleptics, hypothalamic-pituitary disorders, vascular and cardiovascular diseases, dystonia, dyskinesia, hyperkinesias, dementia, ischemia, movement disorders, hypertension and diseases caused by hyperactive immune system, such as allergies and inflammations in mammals, including human beings.

The development of medicinal preparations for treatment of disorders caused by disturbances in functions of the nitrergic and dopaminergic systems by normalization of these systems is of current importance.

Known in the art are tricyclic amines with central dopaminergic activity (U.S. Pat. No. 4,612,316, A), as well as carboxymide dihydropyridine, dihydroquinoline and carboxymide isoquinoline (U.S. Pat. No. 4,727,079, A), new derivatives aminotriazoles andaminooxazoles (U.S. Pat. No. 4,904,676, A), having specific brain-specific dopaminergic activity.

Known in the art is application of benzothiopyranopyridinons for induction of antipsychotic, antidepressant and anti-dopaminergic activity in warm-blooded animals (U.S. Pat. No. 4,547,507, A).

Also known in the art is application of phenoldopam 4', 8-bis-bisulfate and its salts as drugs with pro-dopaminergic activity (U.S. Pat. No. 4,600,714, A).

A proposal is made to use (1,2,5,6- tetrahydro-1-alkyl-3-pyridonyl)-2-thiaazolamines and 4-(hexahydro-1-alkyl-3-pyridinyl)-2-thiaazolamines with anticipated antipsychotic activity for treatment of psychosis, high blood pressure, Parkinson's disease, hyperprolactinemia, sexual disorders and acromegalia (U.S. Pat. No. 46,508,054, A).

Also known in the art are substituted 1-(alkoxyphenyl) piperazine or partial agonists of dopamine, which are offered for treatment of dopamine regulation disorders and treatment of Parkinson's disease, schizophrenia and drug addiction (U.S. Pat. No. 5,281,594, A).

There are also proposed derivative of benzimidazolone with the central dopaminergic activity (U.S. Pat. No. 5,889, 010, A; U.S. Pat. No. 5,883,094, A), as well as N,N'-disubstitiued derivatives benzimidazolone (U.S. Pat. No. 6,521,623, A), which probably can be used for treatment of a wide spectrum of diseases of the nervous system.

The above analogs present only data on binding of appropriate compounds with dopamine receptors, however, in no case the specific therapeutic activity has been proved in animal models or in clinical tests.

DISCLOSURE OF THE INVENTION

An object of the present invention is to create a medicinal agent for correction of disorders of nitrergic and dopaminergic systems and disorders caused by disturbances of these systems, in particular, diseases of the nervous and cardiovascular systems, including disorders caused by drugs abused, disorders of cognitive function and of psychophysiological status.

In the process of development of the present invention a task was set up to find a biologically active compound capable of normalizing the activity of both the nitrergic and dopaminergic systems by controlling the NO level in a cell due to correction of the activity of various isoforms of the NO-synthase, as well as by binding the excessively formed active forms of nitrogen, in particular, peroxynitrite or NO-radical.

The biologically active compounds having properties necessary for solving the specified task, cyclic bioisosteres of derivatives of a purine system having a general formula:

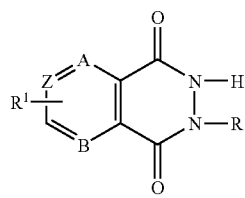

where R=Li, Na K,

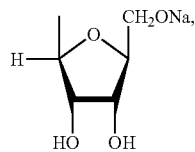

R$^1$=—H, —NH$_2$, —Br, —Cl, —OH, —COOH,
B=—N=, —CH=, Z=—CH=, —N=,
A=—N= at B=—N=, Z=—CH—,
A=—CH= at B=—N=, Z=—CH—,
A=—CH= at B=—N=, Z=—N=,
A=—CH= at B=—CH=, Z=—CH=,
A=—CH= at B=—CH=, Z=—N=, and their pharmacologically acceptable salts having normalizing effect on the endocellular processes, in particular, on the nitrergic mechanisms of the cells (PCT/RU03/00346). The inventors have assumed that the condensed pyridazinedione systems have specific neurotropic activity, and the positive effect is associated with normalization by these compounds of the disturbed functions of the nitrergic and dopaminergic systems.

The mechanisms of influence of the cyclic bioisosteres of derivatives of a purine system on the nitrergic system may involve changes of pH in the cell affecting the activity of nitric oxide synthase, direct interaction of these compounds with nitric oxide and peroxynitrite in the cell and outside the cell, that has an effect both on the nitrergic system as a whole and on the free-radical homeostasis of a biological object. The specified compounds can also differentially modulate activity of various isoforms of nitric oxide synthase that substantially provides a change in the functional condition of cells, organs, tissues and, finally, of the whole organism. The influence of the compounds according to the invention on the dopamine system can be provided due to a change of the distribution of the electron density in the protein molecules of dopamine receptors or due to a change in the properties of membranes surrounding the receptors. The additional influence of these compounds on the other types of receptors, for example, adenosine, can indirectly modulate the activity of the dopamine receptors.

There were investigated derivatives of pyrido [2,3-d]-6H-pyridazine-5,8-dione, cyclic bioisostere derivatives of purine systems, in which the pyridine ring condensated with a pyridazinedione ring having a general formula:

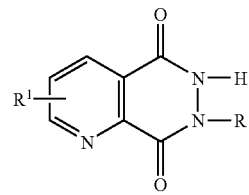

where R=

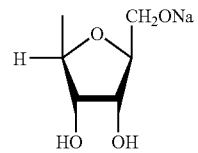

atom Li, Na, K,
R$^1$=—H, —NH$_2$, —Br, —OH, —COOH, in particular:
sodium salt of 7-(β-D-ribofuranosile)pyrido[2,3-d]-6H-pyridazine-5,8-dione (1),
sodium salt of 4-amino-7-(β-D-ribofuranosile)pyrido[2,3-d]-6H-pyridazine-5,8-dione (2),
sodium salt of 3-bromine-7-(β-D-riboftiranosile)pyrido[2,3-d]-6H-pyridazine-5,8-dione (3),
isodium salt of 4-hydroxy-7-(β-D-ribofuranosile)pyrido[2,3-d]-6H-pyridazine-5,8-dione (4),
disodium salt of 3-carboxy-7-(β-D-ribofuranosile)pyrido[2,3-d]-6H-pyridazine-5,8-dione (5),
lithium salt of pyrido [2,3-d]-6H-pyridazine-5,8-dione (6),
sodium salt of pyrido [2,3-d]-6H-pyridazine-5,8-dione (7),
potassium salt of pyrido [2,3-d]-6H-pyridazine-5,8-dione (8).

The derivatives of benzo[d]-3H-pyridazine-1,4-dione, cyclic bioisostere of derivatives of a purine system were investigated, in which the benzene ring is condensed with a pyridazinedione ring having a general formula:

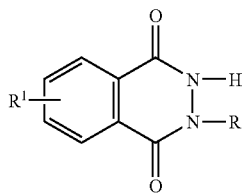

where R=

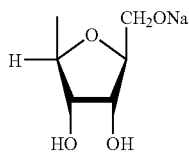

atom Li, Na, K,
R¹=—H, —NH₂, —Cl, —OH, —COOH, in particular:
sodium salt of 2-(β-D-ribofuranosile)benzo[d]-3H-pyridazine-1,4-dione (9),
sodium salt of 5-amino-2-(β-D-ribofuranosile)benzo[d]-3H-pyridazine-1,4-dione (10),
sodium salt of 6-amino-2-(β-D-ribofuranosile)benzo[d]-3H-pyridazine-1,4-dione (11),
sodium salt of 5-chlorine-2-(β-D-ribofuranosile)benzo[d]-3H-pyridazine-1,4-dione (12),
disodium salt of 5-hydroxy-2-(β-D-ribofuranosile)benzo[d]-3H-pyridazine-1,4-dione (13),
lithium salt of 5-amino-benzo[d]-3H-pyridazine-1,4-dione (14),
sodium salt of 5-amino-benzo[d]-3H-pyridazine-1,4-dione (15),
potassium salt of 6-amino-benzo[d]-3H-pyridazine-1,4-dione (16),
disodium salt of 5-hydroxy-benzo[d]-3H-pyridazine-1,4-dione (17),
disodium salt of 6-carboxy-benzo [d]-3H-pyridazine-1,4-dione (18).

Derivative also were investigated pyrazino [2,3-d]-6H-pyridazine-5,8-dione, the cyclic bioisostere derivative of purine systems, in which pyrazinering a ring condensated with pyridazinedione, having a general formula:

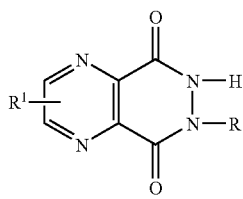

where R=

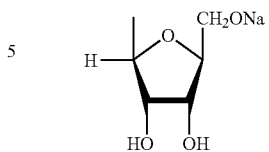

atom Li, Na, K,
R¹=—H, —NH₂, —Cl, —OH, —COOH, in particular:
sodium salt of 7-(β-D-ribofuranosile)pyrazino[2,3-d]-6H-pyridazine-5,8-dione (19),
sodium salt of 2-amino-7-(β-D-ribofuranosile)pyrazino[2,3-d]-6H-pyridazine-5,8-dione (20),
sodium salt of 3-amino-7-(β-D-ribofuranosile)pyrazino[2,3-d]-6H-pyridazine-5,8-dione (21),
sodium salt of 3-bromine-7-(β-D-ribofuranosile)pyrazino[2,3-d]-6H-pyridazine-5,8-dione (22),
disodium salt of 2-hydroxy-7-(β-D-ribofuranosile)pyrazino[2,3-d]-6H-pyridazine-5,8-dione (23),
disodium salt of 2-carboxy-7-(β-D-ribofuranosile)pyrazino[2,3-d]-6H-pyridazine-5,8-dione (24),
lithium salt of pyrazino[2,3-d]-6H-pyridazine-5,8-dione (25),
lithium salt of pyrazino[2,3-d]-6H-pyridazine-5,8-dione (26),
potassium salt of 3-bromine-pyrazino[2,3-d]-6H-pyridazine-5,8-dione (27),
sodium salt of 2-amino-pyrazino[2,3-d]-6H-pyridazine-5,8-dione (28).

The derivatives of pyrimido [4,5-d]-6H-pyridazine-5,8-dione, cyclic bioisostere of derivatives of a purine system were investigated, in which a pyrimidine ring is condensed with a pyridazinedione ring having a general formula:

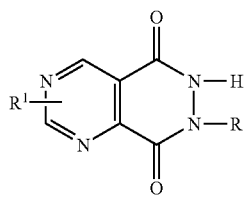

where R=

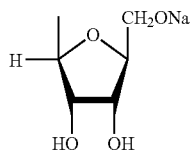

atom Li, Na, K,
R¹=—H, —NH₂, —Cl, —OH, —COOH, in particular:
sodium salt of 7-(β-D-ribofuranosile)pyrimido[4,5-d]-6H-pyridazine-5,8-dione (29),
sodium salt of 2-amino-7-(β-D-ribofuranosile)pyrimido[4,5-d]-6H-pyridazine-5,8-dione (30), sodium salt of 4-amino-7-(β-D-ribofuranosile)pyrimido[4,5-d]-6H-pyridazine-5,8-dione (31), sodium salt of 2-bromine-7-(β-D-ribofuranosile)pyrimido[4,5-d]-6H-pyridazine-5,8-dione (32), sodium salt of 4-hydroxy-7-(β-D-ribofuranosile)pyrimido[4,5-d]-6H-pyridazine-5,8-dione (33), sodium salt of 4-carboxy-7-(β-D-ribofuranosile)pyrimido[4,5-d]-6H-pyridazine-5,8-dione (34), lithium salt of pyrimido[4,5-d]-6H-pyridazine-5,8-dione (35), sodium salt of 2-amino-pyrimido[4,5-d]-6H-pyridazine-5,8-dione (36), potassium salt of 4-bromine-pyrimido[4,5-d]-6H-pyridazine-5,8-dione (37).

Compounds 1-8, which are derivatives of pyrido[2,3-d]-6H-pyridazine-5,8-dione, were obtained by condensation of ortho-dicarboxysubstituted pyridines with hydrazine hydrate in an acetic acid medium (Taguchi Hiroshi. "A new fluorometric assay method for quinolinic acid". Analitic Biochemistry, 1983, 131 (1), p. 194-197).

Compounds 9-18, which are derivatives of benzo[d]-3H-pyridazine-1,4-dione (phthalazine dione), were obtained by condensation of ortho-phthalic acid with hydrazine hydrate in an acetic acid medium (Huntress E. H., Stanley L. N., Parker A. S. "The preparation of 3-Aminophtalhydrazide for use in the Demonstration of Chemiluminescence", J, Am. Chem. Soc., 1994, v. 56, p. 241-242).

Compounds 19-28, which are derivatives of pyrazine[2,3-d]-6H-pyridazine-5,8-dione, were obtained by condensation of ortho-dicarboxysubstituted pyrazines with hydrazine hydrate in an acetic acid medium (Zyczynska-Baloniak I., Czajka R., Zinkowska E., "Synthesis of Derivatives of 4-Hydroxypyrazine-[2,3-d]pyridazine-1-one. Polish Journal of Chemistry. 1978, v. 52, p. 2461-2465; Kormendy K., Ruff F. "Pyridazines condensed with a Heteroring. III"., Acta Chimika Hungarika. 1990, 127 (2), p. 253-262).

Compounds 29-37, which are derivatives of pyrimido[4,5-d]-6H-pyridazine-5,8-dione, were obtained by condensation of ortho-dicarboxysubstituted pyrimidines with hydrazine hydrate in an acetic acid medium (Yurugi S., Hieda M. "Studies on the synthesis of N-Heterocyclic Compounds". Chemistry, Pharmaceutic Bull., 1972, v. 20 (7), p 1522-1527. ibid., p. 1513-1521).

The object of the invention was obtained by determining the biological activity of the above-mentioned cyclic bioisosteres of a purine system and their pharmacologically acceptable salts on nitrergic and dopaminergic mechanisms of cells of an organism having disorders in such systems.

The invention is further illustrated by the following examples, which do not limit the scope of the invention and describe experiments in vivo on models of various disorders caused by dusturbances of nitrergic and dopaminergic in an organism of animals.

1. The Effect of the Compounds According to the Invention on Disorders Caused Morphine Abstinence.

The effects of compounds Nos 1, 4, 6, 10, 11, 18, 21, 24, 26, 32, 35, 37 according to the invention on the behavioral characteristics as well as on the nitrergic system of animal brain were studied using a known model of physical dependence from morphine (morphine abstinence), a recognized model of human heroin abstinence.

The physical dependence on morphine was produced on 27 groups of male 6 month old Wistar rats weighing 250-350 g:
the animals of group No. 1 (n=7) were not injected with morphine, and they served a control group, the animals of group No. 2 (n=7) were injected with morphine hydrochloride up to the appearance of a pronounced abstinence syndrome, the animals of groups Nos. 3-14 (n=7) were injected with one of compounds of the pyridopyridazine series-1 or 4 or 6 according to the invention (groups Nos. 3, 4, 5), or one of compounds of the benzopyridazinedione series-10 or 11 or 18 according to the invention (groups Nos. 6, 7, 8), or one of compounds of the pyrazinepyridazinedione series-21 or 24 or 26 according to the invention (groups Nos. 9, 10, 11), or one of compounds of the pyrimidinepyridazinedione series-32 or 35 or 37 (groups Nos. 12, 13, 14), the animals of groups Nos. 15-26 (n=7) were injected with of morphine hydrochloride to the point of the development of a pronounced abstinence syndrome and then: in each group-one of the compounds according to the invention by a scheme similar to that for groups Nos. 3-14.

Morphine hydrochloride was administered by intraperitoneal injection according to a modified scheme: within 6 days two times a day (at 10.00 and 20.00) in increasing doses from 10 to 100 mg/kg: the 1st day-10 mg/kg, the 2nd day-20 mg/kg, the 3rd day-40 mg/kg, the 4th day-60 mg/kg, the 5th day 80 mg/kg, the 6th day -100 mg/kg. The injections of compounds according to the invention were performed three times intramuscularly at a dose of 20 mg/kg at a day following the last dose of morphine. (Dum J, Blasig J, Herz A: Buprenorphine: demonstration of physical dependence liability. Eur. J. Pharmacol., 1981, V. 70, p. 293-300.; Rahman S., Ali Khan R., Kumar A. Experimental study of the morphine de-addiction properties of Delphinium denudatum Wall, BMC Complement Altern. Med., 2002, V.29, p.1-6). Thirty six hours after the last injection selected motor and autonomice parameters which are specific symptoms of abstinence were monitored in the <<open field>> test (an arena with a diameter of 120 cm and wall height of 40 cm).

The expression of the abstinence syndrome was estimated within 5 minutes using a number of signs specific to the syndrome: <<wet dog>> shakes, convulsions, mastication, teeth scratch, forelimb jogging, and autonomic signs: diarrhea, ptosis, rhinorrhea, piloerection, dyspnea, squeak at touching, aggression (Blasig J., Herz A., Reinhold K., Zieglgansberger S. Development of physical dependence on morphine in respect to time and dosage and quantification of the precipitated withdrawal syndrome in rats. Psychopharnacologia, Berlin, 1973, V.33, p.19-38; Rahman S., Ali Khan R., Kumar A. Experimental study of the morphine de-addiction properties of Delphinium denudatum Wall, BMC Complement Altern. Med., 2002, V.29, p.1-6.). The observable signs were recorded quantitatively (if it was possible) with further assignment of an index to each sign (depending on the specific feature of the sign) and calculation of the sum of scores. The expression of the abstinence syndrome was presented as a sum of scores. The results were processed using nonparametric statistical analysis based on the Mann-Whitney test. A graph presenting effects of morphine and compounds according to the invention on behavioral reactions of investigated animals is shown in FIG. 1, where the effect is calculated as average for series of compounds, M of numbers on the basis of the specified indexes of the abstinence syndrome for animal groups Nos. 1-27. The average relative data are given in Table 1.

TABLE 1

Effect of compounds according to the invention on the development of morphine abstinence

| Specific signs of abstinence | Index | Control – morphine | Authentic differences ξ-square criterion) in appearance of signs of abstinence | | | |
|---|---|---|---|---|---|---|
| | | | Morphine- (morphine + compound 1 or 4 or 6) | Morphine- (morphine + compound 10 or 11 or 18) | Morphine- (morphine + compound 21 or 24 or 26) | Morphine- (morphine + compound 32 or 35 or 37) |
| <<Wet dog>> shakes | 2 | 0.0002 | 1.0000 | 0.7562 | 0.7821 | 1.0000 |
| Convulsions | 2 | 0.0507 | 0.7821 | 0.7546 | 0.3456 | 0.5578 |
| Mastication | 2 | 0.0308 | 0.1888 | 0.1032 | 0.1975 | 0.1888 |
| Grit with teeth | 2 | 0.1266 | 0.7144 | 0.8652 | 0.2994 | 0.7003 |
| Forelimb jogging | 2 | 0.0180 | 0.7821 | 0.8217 | 0.6745 | 0.9321 |
| Squeak when touched | 1 | 0.0053 | 0.1888 | 0.1342 | 0.1968 | 0.2035 |
| Diarrhea | 1 | 0.0075 | 0.0046 | 0.0032 | 0.0067 | 0.0001 |
| Ptosis | 2 | 0.0053 | 0.0201 | 0.0320 | 0.0105 | 0.0232 |
| Rhinorrhea | 3 | 0.2994 | 0.3017 | 0.4032 | 0.2131 | 0.2935 |
| Piloerection | 2 | 0.5770 | 0.1847 | 0.2567 | 0.2567 | 0.2345 |
| Dyspnea | 2 | 0.0053 | 0.0722 | 0.0834 | 0.0567 | 0.0685 |
| Aggression | 1 | 0.5770 | 0.8327 | 0.8456 | 0.7921 | 0.8456 |

From Table 1 it is clear that from the signs characterizing development of the abstinence syndrome, the compounds according to the invention effectively stopped the diarrhea, ptosis and dyspnea. They also had an effect on the convulsive activity caused by cancellation of morphine.

Thus, we have revealed some components of morphine abstinence sensitive to the correction by the compounds according to the invention.

2. The Effects of Compounds According to the Invention on Nitrergic Indexes in Brain.

2.1. Preparation of Material for Biochemical Studies

After the above experiments the rat brains were isolated and immediately placed in the ice cold 0.9% solution of sodium chloride. After cooling the following structures were isolated from the brain: cerebral cortex, hippocampus, mesencephalon, striatum, brainstem, hypothalamus and cerebellum. The isolated tissue was homogenized in a Potter S homogenizer for 3 minutes at 1500 rpm in 4-5 volumes of 20 mM HEPES (pH 7.5) at 4° C. The supernatants were centrifuged for 30 minutes at 11000 g at 4° C., and aliquots of the obtained supernatants were taken for determining nitrates and nitrites (NOx-), while the remaining part was mixed with cooled 20 mM of HEPES (pH 7.5), containing 0.5 mM ethylenediamine tetraacetate (EDTA), 1 mM dithiotreitol (DDT), 1 mM phenylmethylsulfonyl fluoride (PMSF), aprotinine and leupeptine at a concentration of 5 µg/ml, this mixture being used for determining nitric oxide synthase (NOS) activity.

2.2. Measurement of Nitrates/Nitrites (NOx-)

To estimate the intensity of metabolism of nitric oxide in rats, quantitative determination of stable metabolites of nitrogen oxide-nitrites and nitrates (NOx-) was performed using a fluorometric method by fluorescence of naphthotriazole, a product of reaction of 2,3- diaminonaphthalene (DAN) and nitrite in an acidic medium (Misko T. R., Schilling R. J., Salvemini D. et al. A fluorometric assay for the measurement of nitrite in biological samples. Anal. Biochem., 1993, V. 214, p.11-16) with modifications (Lei B., Adachi N., Nagaro T., Arai T. Measurement of total nitric oxide metabolite (NO (x) (-)) levels in vivo. Brain. Res. Protoc., 1999, V. 4, p. 415-419).

The supernatants of brain deproteinized at 100° C. were placed in a nitrite recovery system containing 0.125 unit/ml of nitrate reductase, 25 µM NADPH and 25 µM FAD prepared in 20 mM Tris-HCl buffer pH 7.6 and incubated for 30 minutes at 37° C. For oxidation of NADPH a lactate dehydrogenase (LDH)/pyruvate system was used. Then 316.0 µM DAN solution in 0.62 M HCl was added and the mixture was incubated for 10 minutes in dark. For stabilization of fluorescence of the formed naphthotriazole, 280 mM NaOH was added. The fluorescence intensity was measured using spectrofluorometer Hitachi F-3000 at a wavelength of excitation 365 nm and emission 405 nm. To calculate the concentration of NOx- in the brain a standard solution of sodium nitrate was used. The concentration of NOx- was expressed in nmol/mg of protein.

2.3. Determination of Nitric Oxide Synthase Activity

The activity of nitric oxide synthase (NOS) was determined using a radiometric method by the rate of L-citrulline accumulation in a reaction of [$^3$H] L-arginine oxidation catalyzed by NOS (Bredt M., Snyder S. Nitric oxide mediates glutamate-linked enhancement of cGMP levels in the cerebellum. Proc. Natl. Acad. Sci., USA, 1989, V.86, p.9030-9033). The formation of L-citrulline in this reaction is equivalent to a biosynthesis of nitric oxide.

The reaction was initiated by adding brain supernatant in the reaction medium containing 2 µCi/ml of [3H] L-arginine, 20 mM HEPES (pH 7.4), 0.2 mM $CaCl_2$, 5 µM FAD, 5 µM FMN, 1 mM NADPH, 50 µM of $BH_4$. After 15-60 minutes of incubation at 37° C. a suspension of Dowex 50WX8-400 ($Na^+$-form), which sorbs unreacted [$^3$H]L-arginine, but not [$^3$H] L-citrulline was added to the samples. After the sorption the radioactivity of the samples was determined on a scintillation counter SL-4000 ("Intertechnique"). The activity of $Ca^{2+}$-dependent and $Ca^{2+}$-independent NOS isoforms was determined by the difference of rates of [$^3$H]L-citrulline formation in three parallel samples containing 2 mM EDTA ($Ca^{2+}$ chelator), 2 mM EDTA+2 mM L-NAME (inhibitor all NOS isoforms) or without inhibitors. The enzyme activity was expressed in rnol [$^3$H]L-citrulline acumulated per 1 minute on 1 mg of supernatant protein.

2.4. Quantification of Protein

The content of protein in the samples was determined by the Bradford method (Bradford M. M. A rapid and sensitive method for quantitation of microgram quantities of protein using the principle of protein binding . Anal. Biochem., 1976, V. 72, p. 248-254) using Coumassi dye. The statistical analysis was performed using methods appropriate for respective experiments. The data are expressed as mean±standard error of mean.

system of the brain. It is well known that a non-selective D1/D2 agonist apomorphine in low doses causes penile erection in rodents (Giuliano F., Allard J. Dopamine and male sexual function. Eur. Urol., 2001, 40 (6), 601-608; Giuliano F., Allard J., Rampin O. et. al. Pro-erectile effect of systemic apomorphine: existence of a spinal site action. J. Urol., 2002, 167 (1), 402-406; Brien S. E., Smallegange C., Gofton W. T., et. al. Development of a rat model of sexual performance anxiety: effect of behavioral and pharmacological hyperadr-

TABLE 2

Effects of morphine and compounds according to the invention on the brain nitrergic system

| Index in the brain region | Group No. 1 control | Group No. 2 (morphine) | Groups Nos. 3-14 (Compound from group 1, 4, 6, 10, 11, 18, 21, 24, 26, 32, 35, 37) | Groups Nos. 15-17 (Morphine + compound 1 or 4 or 6) | Groups Nos. 18-20 (Morphine + compound 10 or 11 or 18) | Groups Nos. 21-23 (Morphine + compound 21 or 24 or 26) | Groups Nos. 24-27 (Morphine + compound 32 or 35 or 37) |
|---|---|---|---|---|---|---|---|
| | | | Nitrites, nmol/mg of protein: | | | | |
| cerebral cortex | 4.63 ± 0.29 | 5.31 ± 0.29 | 4.31 ± 0.37 | 4.72 ± 0.37 | 4.93 ± 0.39 | 4.62 ± 0.27 | 4.84 ± 0.31 |
| cerebellum | 6.37 ± 0.64 | 6.07 ± 0.42 | 6.66 ± 0.63 | 5.46 ± 0.44 | 5.85 ± 0.47 | 5.76 ± 0.49 | 5.93 ± 0.54 |
| brainstem | 8.24 ± 1.02 | 7.63 ± 0.96 | 6.31 ± 0.58 | 6.57 ± 0.72 | 6.99 ± 0.82 | 7.07 ± 0.85 | 6.87 ± 0.81 |
| striatum | 7.25 ± 0.66 | 4.92 ± 0.43 | 6.11 ± 0.29 | 3.57 ± 0.42 | 3.57 ± 0.42 | 3.57 ± 0.42 | 3.57 ± 0.42 |
| hippocampus | 4.39 ± 0.23 | 6.45 ± 0.69 | 6.47 ± 0.72 | 5.44 ± 0.43 | 5.24 ± 0.49 | 5.27 ± 0.41 | 5.31 ± 0.33 |
| midbrain | 5.66 ± 0.19 | 9.41 ± 1.20 | 6.65 ± 0.70 | 5.50 ± 0.48 | 5.75 ± 0.39 | 5.99 ± 0.58 | 5.95 ± 0.52 |
| hypothalamus | 6.57 ± 0.50 | 4.62 ± 0.71 | 6.77 ± 0.83 | 6.57 ± 0.88 | 6.91 ± 0.58 | 6.87 ± 0.75 | 6.77 ± 0.46 |
| | | | Activity of NOS, nmol/min/mg of protein: | | | | |
| striatum | 1.73 ± 0.07 | 1.19 ± 0.14 | 1.26 ± 0.08 | 1.24 ± 0.08 | 1.29 ± 0.09 | 1.21 ± 0.10 | 1.34 ± 0.09 |
| midbrain | 2.18 ± 0.09 | 3.08 ± 0.09 | 2.60 ± 0.29 | 1.83 ± 0.23 | 1.99 ± 0.29 | 2.03 ± 0.31 | 1.89 ± 0.27 |
| hippocampus | 2.55 ± 0.12 | 3.10 ± 0.20 | 3.09 ± 0.16 | 2.70 ± 0.14 | 2.51 ± 0.19 | 2.33 ± 0.11 | 2.65 ± 0.15 |
| hypothalamus | 5.37 ± 0.20 | 3.42 ± 0.54 | 5.45 ± 0.24 | 5.26 ± 0.28 | 5.36 ± 0.33 | 5.47 ± 0.32 | 5.56 ± 0.34 |

As it is evident from the results listed in Table 2, in the brain morphine results in the accumulation of nitrites and modulation of NOS activity: a decrease in the nitrergic indices was observed in the striatum and hypothalamus, and an increase in the midbrain and hippocampus ($P<0.05$; $P=0.1$ for nitrites in hypothalamus, T-test). The compounds according to the invention normalized the activity of NOS, impaired by morphine in the hypothalamus, midbrain and hippocampus.

Conclusions

The compounds according to the invention injected repeatedly three times at a dose of 3×20 mg/kg intramuscularly, exert the following effects in the morphine withdrawal syndrome:
  reduces the development of abstinence syndrome, in particular, such components of behavioral disorder, as a diarrhea, ptosis and dyspnea;
  improves the psychophysiological status due to antidepressive effect when inhibiting the abstinence syndrome;
  has differential and specific effects on different isoforms of nitric oxide synthase performing correction of the disturbed nitrergic mechanisms in the brain regions.

These data provide evidence for promising aspects of application of the compounds according to the invention for treatment of disorders caused by substances abuse, in particular, narcotics.

3. Effects of the Compounds According to the Invention on Impairments of Sexual Function Associated with Disorders of Dopaminergic of System.

One of the mechanisms regulating the sexual function of mammals is associated with functioning of the dopaminergic energic stimulation on apomorphine-induced erections. Int. J. Impot. Res., 2002, 14 (2), 107-115.). In this connection, we have studied the effects of the compounds according to the invention on apomorphine-dependent erection in rats.

Nine groups of adult male Wistar rats weighing 350-450 g maintained at the normal (not inverted) light cycle were used in the experiments. To study the effect of the compounds on the sexual function, low-potency animals with a single erection were selected. Control group No. 1 (n=7) was composed of animals not injected with the compounds according to the invention. The animals of groups Nos. 2-9 (n=7) were injected with one of the compounds according to the invention selected from the group of compounds 2, 8, 9, 15, 19, 25, 31, 36, intraperitoneally in a course of 5 injections at a dose of 10 mg/kg with an interval between the injections 48 hours. Apomorphine was dissolved in 0.1% aqueous solution of ascorbic acid and then was injected to all animal subcutaneously at a dose of 0.1 mg/kg during 24-28 hours after the last injection of the compounds according to the invention. The monitoring of sexual activity was made individually for each animal immediately after the administration of apomorphine; the monitoring time was 20 minutes. The following indices were registered: the time of beginning of the first erection, time intervals between the erections, the number of erections for the entire period of observation.

The statistical analysis of the results was made using T-test and ξ-square test. The results are given in Table 3 as means±standard error of means.

TABLE 3

The effect of the compounds according to the invention on disorders of sexual function of rats

| Group (experimental conditions) | Latent period of first erection, minutes | Number of erection for the entire period of observation | Time between $1^{st}$ and $2^{nd}$ erections, minutes | Time between 3rd and $2^{nd}$ erections, minutes |
|---|---|---|---|---|
| No. 1 (Control + apomorphine) | 6.63 ± 0.99 | 2.00 ± 0.37 | 4.60 ± 0.53 | 5.90 ± 0.87 |
| Nos. 2-3 (Compound 2 or 8 + apomorphine) | 5.21 ± 0.30 $P = 0.1$ | 3.13 ± 0.35 $P < 0.05$ | 3.94 ± 0.60 | 5.52 ± 1.14 |
| Nos. 4-5 (Compound 9 or 15 + apomorphine) | 5.09 ± 0.27 $P < 0.1$ | 3.24 ± 0.39 $P < 0.05$ | 3.87 ± 0.59 | 5.19 ± 0.78 |
| Nos. 6-7 (Compound 19 or 25 + apomorphine) | 5.24 ± 0.19 $P < 0.1$ | 3.29 ± 0.27 $P < 0.05$ | 3.75 ± 0.64 | 5.12 ± 0.87 |
| Nos. 8-9 (Compound 31 or 36 + apomorphine) | 5.12 ± 0.24 $P < 0.1$ | 3.32 ± 0.31 $P < 0.05$ | 3.34 ± 0.69 | 5.02 ± 1.01 |

From the results of the investigation given in Table 3 it is obvious that the compounds according to the invention reliably increase the number of erections of the animals (more than 1.5 times) and demonstrated a statistically significant trend to a decrease of the latent period of the first erection 1.3 times.

Conclusions

Thus, beneficial effects of the compounds according to the invention on the sexual function of rats has been proved.

Since the used model involves certain cerebral mechanisms, we may consider that the mechanism of action of the compounds according to the invention is associated with its effect on the dopaminergic system of the brain, in particular, by correcting the dysfunction of D1/D2 dopamine receptors. From the results obtained it is apparent that the compounds according to the invention can also be used for correction of numerous pathologies of the nervous system associated with dysfunction of the dopaminergic system.

4. Effects of the Compounds According to the Invention on Cognitive Function and Psychophysiological Status of Animals A screening test was conducted to evaluate effects of the compounds according to the invention on processes of learning and memory, as well as on the psychophysiological status of rats.

4.1. Experimental Procedure

Wistar rats weighing 220-300 g were used for the study. In each test control group of rats No. 1 (n=10) and experimental groups Nos. 2-9 (n=10) were used.

The animals of groups Nos. 2-9 were injected with one compound from the group of compounds Nos. 2, 7, 11, 17, 20. 28, 29, 35 according to the invention intramuscularly at a single dose of 10 mg/kg. The drugs were dissolved in neutralized water. To study the effect of the compounds according to the invention, conventional tests were used for evaluation of learning and memory: active avoidance, passive avoidance and of psychophysiological status: anxiety, aggression, depression. These tests are usually used for screening of nootropic and psychopharmacological medications, as well as for study of various effects on the cognitive and emotional sphere.

4.1.1. Evaluation of the Ability to Learning and Memory

A conditional reaction of passive avoidance (CRPA) was developed on the basis of a single electrocutaneous reinforcement in a setting consisting of two chambers: a large illuminated chamber (25×25×25 cm) and a small dark chamber (17.5×14×14 cm) with an electrified floor, both chambers communicating through a rectangular pass of 7×10 cm. During the training the rat was placed for 3 minutes in the middle of the illuminated chamber with its tail pointing to the pass into the dark chamber. The animal searched the chamber, found the pass and proceeded into the dark compartment. A rat prefers to stay in dark room because of its biological features. The latent period of the first entry into the dark chamber (T1) was recorded, then the rat was taken off from the dark chamber at once. After 30 minutes the procedure was repeated, and the latent period of the second pass into the dark chamber (T2) was recorded. After another 30 minutes the latent period of the third entry into the dark chamber (T3) was recorded, and the pass was closed by a door (the animal remained inside). Then alternating electric current (50 Hz, 80 V) was applied to the conductive floor for 5 seconds, and after that the rat was taken off and placed into the home cage. The test of retention of the acquired reaction was performed after 24 hours, 7 and 14 days. For this purpose, the rat was placed in the test setting for 3 minutes and the latent period of entry into the dark chamber was recorded. The criterion of learning ability is the latent period of passage of at least 180 seconds. A longer time of stay of the animal in the illuminated part of the setting or refusal to pass into the dark chamber is considered as retention of the acquired reaction.

4.1.2. Evaluation of the Psychophysiological Status (a) Anxiety.

The anxiety is considered as behavior associated with prevalence of fear motivation. Among various kinds of anxiety phobias are prevailing, especially simple phobia and agoraphobia (open-space phobia). Testing rats in an elevated plus maze is one of the most widely used methods to study anxiety in rodents. The maze we have used is made of wood covered with green plastic. The maze consists of two open sleeves (50×15 cm) located opposite to each other, and two closed sleeves of the same size with 20 cm high walls along the long parts of the sleeve. The maze was located at a height of 70 cm above the floor surface. The test was performed in a sound-proof room. The rat was placed in the central part of the setting, and within 10 minutes the observer visually registered the number of entries into the open and closed sleeves of the maze as well as the time spent in the open and closed sleeves. Each animal was tested once.

(b). Depression Depressive states are severe disorders of mental activity characterized by emotional indifference, feelings of misfortune, ideas of death, suicidal manifestations, changes in psychomotor behavior, disorders of cognitive functions (first of all, inability of concentration of attention, memory disorders). One of the most effective and widely used methods for revealing condition similar to depression in animals is the method of forced swimming (Porsolt swimming test). During the test a rat is placed in a vessel with water so that the animal cannot independently get out from the stress situation. The indexes of depression under the test conditions were the number and duration of the periods of passive swimming (staying on the water surface without visible movement of the legs). Such type of reaction reflects condition of behavioral <<despair>>. The experiments were performed in a round basin with a diameter of 40 cm and a height of 50 cm. The basin was filled with water having a temperature of 22° C. and a level of 30 cm. The rat was put in the basin and the following behavior indices were recorded: duration of the first period of active swimming (swimming with chaotic movement of the legs, climbing), duration of passive swimming (periods of suspension without movement), and duration of active swimming. The tests were performed once for 5 minutes. The statistical analysis was made, using in each case suitable statistical tests.

The results of the experiments are shown in FIGS. 2a, 2b, 3a, 3b, 3c, 4a, 4b, where:

FIG. 2a illustrates the latent period tl of the entry into the dark compartment after the electric shock, FIG. 2b illustrates the number N of trained animals; the T0 values are initial N before current application, T1, T7, T14 after 1, 7 and 14 days, respectively;

FIG. 3a shows the number of entries N1 in the open sleeve (area O) and closed sleeve (area C);

FIG. 3b shows the time t spent in the open sleeve;

FIG. 3c shows the number of animals N2 having not entered the open sleeve;

FIG. 4a illustrates the time ts of swimming before the first suspension (area A) and the time ts of active swimming (area B);

FIG. 4b shows the number of suspensions N3.

The results are presented with an mean±standard error of mean.

Visual observation did not reveal any disorders in the behavior or in the appearance of the rats after administration of the preparation therein.

Figure 1:
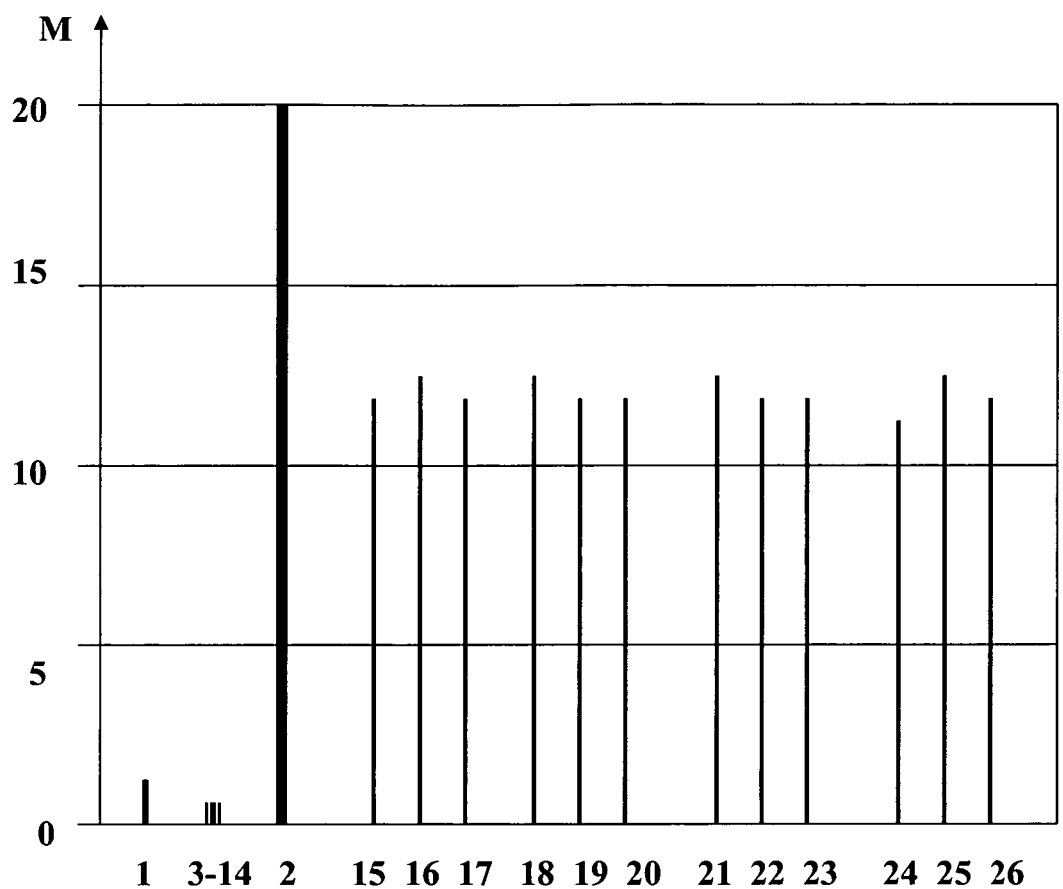
Figure 2A:
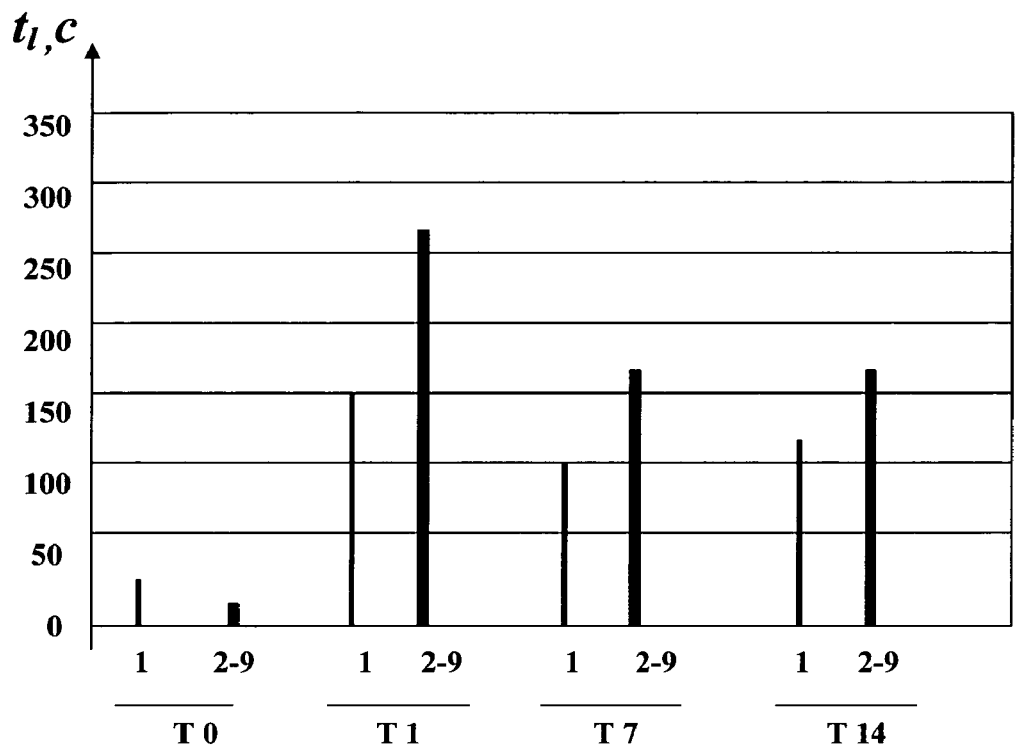
FIG. 2a, 2b illustrates the effect of the compounds according to the invention on learning of conditional passive avoidance reaction for animals of groups Nos. 1-9.
Figure 2B:
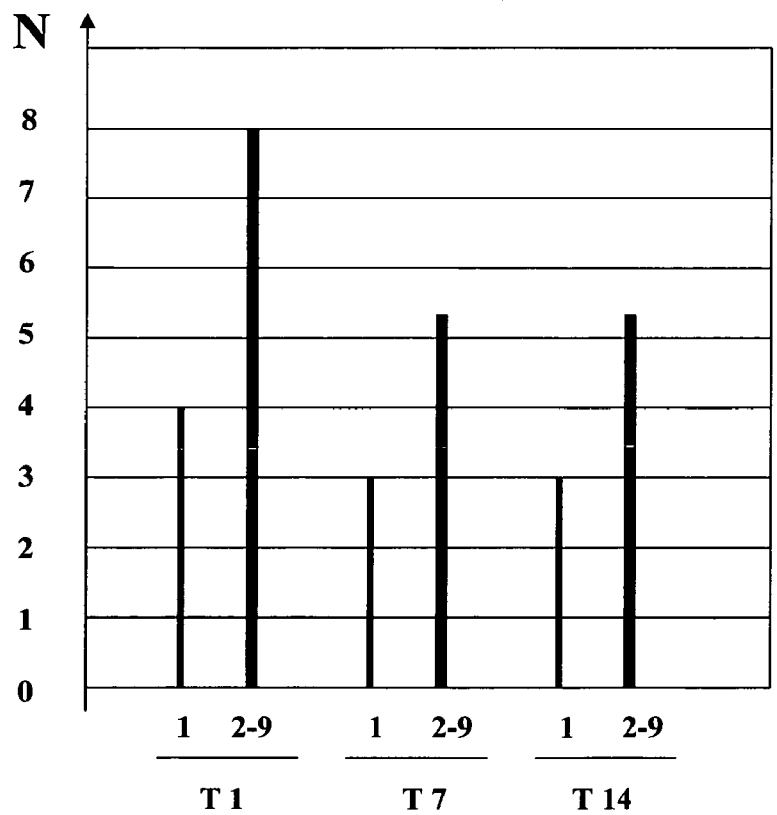

In the test of passive avoidance (FIG. 2a, 2b) the compound according to the invention ($P<0.05$, T-test) increased the latent period tl of the entry into the dark compartment a day after the electric shock (FIG. 2a), this pointing out to more effective working memory of the rat as a result of administration of the preparation. From FIG. 2b it is evident that the number of learned animals N is higher in the group received the compound according to the invention (statistically significant trend, $P<0.07$, $\xi$-square test). In spite of the fact that both the number of trained animals N and the latent period ti were higher in groups Nos. 2-9, administered with the compounds according to the invention than in the control group No. 1, one and two weeks after the test the significance of the differences became nonsignificant.

Figure 3A:
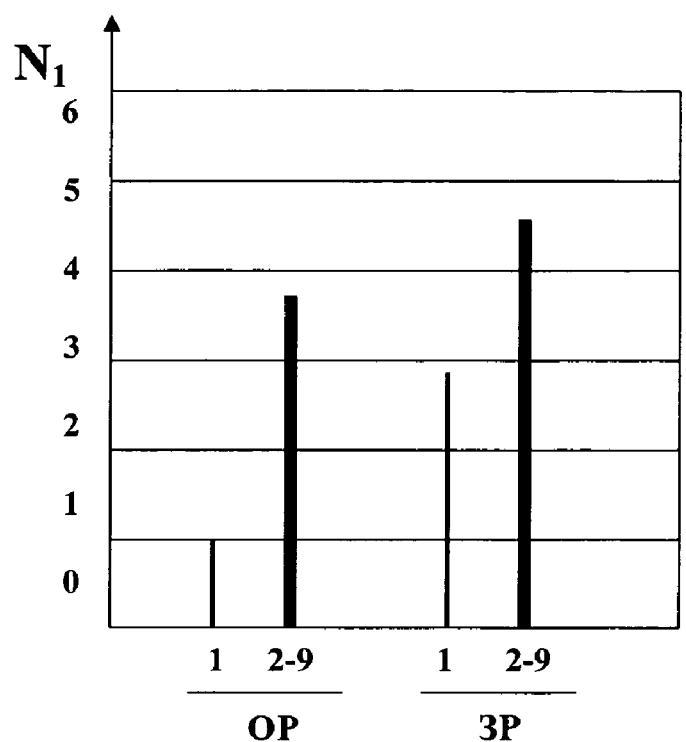
FIG. 3a, 3b, 3c illustrate the effect of the compounds according to the invention on the anxiety of the rats of groups Nos. 1-9 in the elevated plus maze.
Figure 3B:
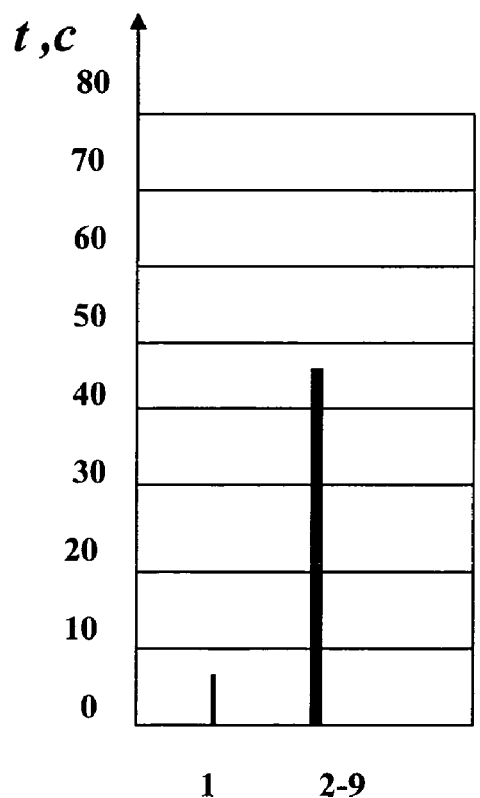
Figure 3C:
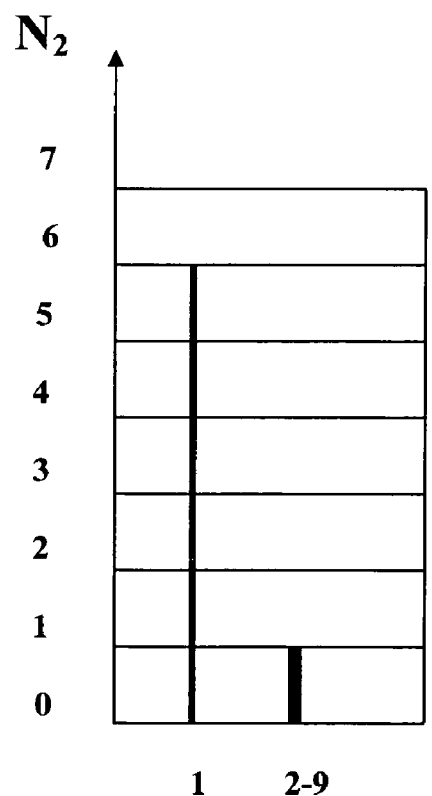

The test for anxiety in the elevated plus maze (FIGS. 3a, 3b, 3c) has revealed a higher exploratory activity (and, hence, lower anxiety) in the groups receiving the compounds according to the invention-the number N1 of entries into the open and closed sleeves was significanltly higher ($P<0.05$, T-test) than in the control group (FIG. 3a), the time t, spent in the open sleeve, being 2,2 times higher in the groups receiving the compound according to the invention (FIG. 3b), although because of variability of the data the differences were only at a level of trend ($P<0.1$, T-test). By the number N2 of animals who did not enter the open sleeve (the animals with the most pronounced anxiety), the control group exceeded the test group by a factor of 6 (6 of 10 and 1 of 10 respectively, $P<0.02$, $\xi$-square test) (FIG. 3c).

Thus, the compounds according to the invention significantly reduced anxiety when testing the animals in the elevated plus maze.

Figure 4A:
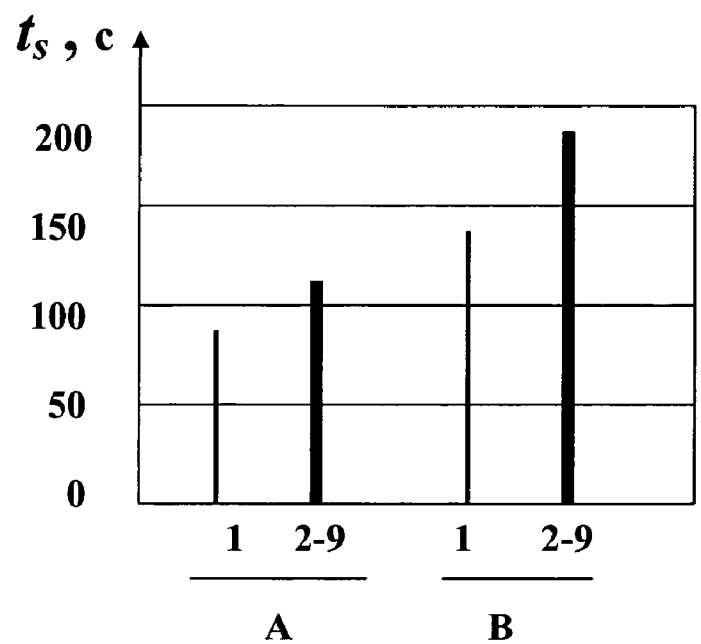
FIG. 4a, 4b illustrate the effect of the compounds according to the invention on the depression of the animals of groups Nos. 1-9 in the Porsolt forced swimming test.
Figure 4B:
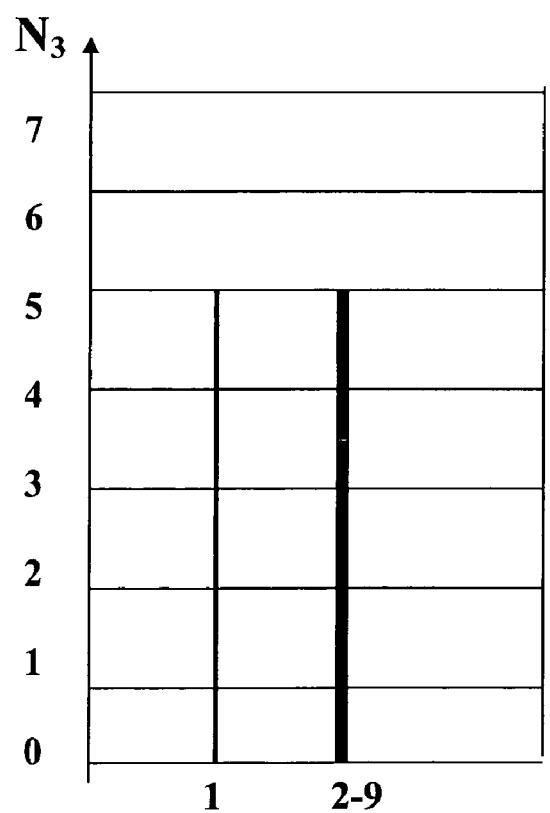

The test for depression (forced swimming) (FIGS. 4a, 4b) has not revealed a significant effect of the compounds according to the invention either by the total time ts of the active swimming (FIG. 4a), or by the number N3 of stationary positions (FIG. 4b). Nevertheless, the rats of groups Nos. 2-9 administered with the compounds according to the invention demonstrated a trend ($P=0.07$, T-test) to an increase of the period ts from the active swimming to the first suspension (time A in FIG. 4a) that may indicate their initially lower depression or higher endurance.

Thus, on the basis of screening of the compounds according to the invention in the tests characterizing the learning and psychophysiological status of the animals, it has been found that the said compounds improve long-term memory in the passive avoidance test, significantly reduce the anxiety of the animals and show a tendency towards a decrease of the depression. In other words, the compounds according to the invention positively influence the capability of the animals to learning (cognitive function) and psychophysiological status of the animals.

Conclusions

Thus, the direct experiments in vivo have shown that the cyclic bioisosteres of derivatives of a purine system modulate the nitrergic and dopaminergic system of animal brain.

It has been shown experimentally that these compounds can be used as neuroprotectors at pathological conditions of nervous system. The administration of the compounds according to the invention improves the cognitive function and psychophysiological status by reducing the anxiety and depression.

The compounds according to the invention significantly improve sexual function and render positive influence in the case of an abstinence syndrome.

Taking into account the mechanism of action of the cyclic bioisosteres of derivatives of a purine system according to the invention and involvement of the dopaminergic and nitrergic systems modulated thereby in pathogenesis of various diseases, we may conclude that the above-mentioned compounds can be used for treatment of a number of diseases, including chemical dependences, i.e. disorders caused by drug abuse, such as dependences on narcotics, alcohol and nicotine, insomnia, sexual disorders (including sexual dysfunction), gastrointestinal disorders, psychoses, affective disorders, inorganic psychoses, personality disorders, psychiatric disorders of mood, schizophrenia and schizoaffective disorders, polydipsia, bipolar disorders, dysphoric mania, anxiety and diseases, associated therewith, obesity, bacterial infections of the central nervous system such, as meningitis, disorders of learning, disorders of memory, Parkinson's disease, depression, extrapyramidal side effects of neuroleptics, hypothalamic-pituitary effects, vascular and cardiovascular diseases, dystonia, dyskinesia, hyperkinesis, dementia, ischemia, motion disorders, hypertension and diseases caused by a hyperactive immune system, such as allergies and inflammations, of mammals and human beings.

The invention claimed is:

1. A method of treating diseases caused by disorders of nitrergic system and/or dopaminergic system of an organism comprising administering an active ingredient having normalizing effect with respect to nitrergic and dopaminergic systems, wherein the active ingredient is present in a pharmaceutically-acceptable carrier in an amount sufficient for effecting said systems, said active ingredient being a cyclic bioisostere of derivatives of a purine system having a general structural formula

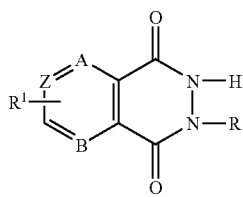

where R is selected from the group consisting of

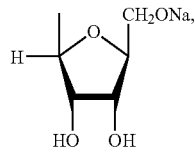

Li, Na, and K;
$R^1$ is selected from the group consisting of —H, —$NH_2$, —Br, —Cl, —OH, and —COOH;
A is selected from the group consisting of —N= and —C=;
B is selected from the group consisting of —N= and —C=;
Z is selected from the group consisting of —C= and —N=;
wherein when A is —N=, then B is —N= and Z is —C=, or pharmacologically acceptable salts thereof.

2. The method as claimed in claim 1, wherein said active ingredient is selected from the group consisting of: sodium salt of 7-(P-D-ribofuranosile)pyrido[2,3-d]-6H-pyridazine-5,8-dione; sodium salt of 4-amino-7-(P-D-ribofuranosile)pyrido[2,3-d]-6H-pyridazine-5,8-dione; sodium salt of 3-bromo-7-(P-D-ribofuranosile)pyrido[2,3-d]-6H-pyridazine-5,8-dione; disodium salt of 4-hydroxy-7-(P-D-ribofuranosile)pyrido[2,3-d]-6H-pyridazine-5,8-dione; disodium salt of 3-carboxy-7-(P-D-ribofuranosile)pyrido[2,3-d]-6H-pyridazine-5,8-dione; lithium salt of pyrido [2,3-d]-6H-pyridazine-5,8-dione; sodium salt of pyrido [2,3-d]-6H-pyridazine-5,8-dione; potassium salt of pyrido [2,3-d]-6H-pyridazine-5,8-dione; sodium salt of 2-(P-D-ribofuranosile)benzo[d]-3H-pyridazine-1,4-dione; sodium salt of 5-amino-2-(p-D-ribofuranosile)benzo[d]-3H-pyridazine-1,4-dione; sodium salt of 6-amino-2-(3-D-ribofuranosile)benzo[d]-3H-pyridazine-1,4-dione; sodium salt of 5-chloro-2-(P-D-ribofuranosile)benzo[d]-3H-pyridazine-1,4-dione; disodium salt of 5-hydroxy-2-(P-D-ribofuranosile)benzo[d]-3H-pyridazine-1,4-dione; lithium salt of 5-amino-benzo[d]-3H-pyridazine-1,4-dione; sodium salt of 5-amino-benzo[d]-3H-pyridazine-1,4-dione; potassium salt of 6-amino-benzo[d]-3H-pyridazine-1,4-dione; disodium salt of 5-hydroxy-benzo[d]-3H-pyridazine-1,4-dione; disodium salt of 6-carboxy-benzo[d]-3H-pyridazine-1,4-dione; sodium salt of 7-(P-D-ribofuranosile)pyrazine[2,3-d]-6H-pyridazine-5,8-dione; sodium salt of 2-amino-7-(P-D-ribofuranosile)pyrazine[2,3-d]-6H-pyridazine-5,8-dione; sodium salt of 3-amino-7-(P-D-ribofuranosile)pyrazine[2,3-d]-6H-pyridazine-5,8-dione; sodium salt of 3-bromo-7-(P-D-ribofuranosile)pyrazine[2,3-d]-6H-pyridazine-5,8-dione; disodium salt of 2-hydroxy-7-(p-D-ribofuranosile)pyrazine[2,3-d]-6H-pyridazine-5,8-dione; disodium salt of 2-carboxy-7-(P-D-ribofuranosile)pyrazine[2,3-d]-6H-pyridazine-5,8-dione; lithium salt of pyrazine[2,3-d]-6H-pyridazine-5,8-dione; sodium salt of pyrazine[2,3-d]-6H-pyridazine-5,8-dione; potassium salt of 3-bromo-pyrazine[2,3-d]-6H-pyridazine-5,8-dione; sodium salt of 2-amino-pyrazine[2,3-d]-6H-pyridazine-5,8-dione; sodium salt of 7-(β-D-ribofuranosile)pyrimido[4,5-d]-6H-pyridazine-5,8-dione; sodium salt of 2-amino-7-(β-D-ribofuranosile) pyrimido[4,5-d]-6H-pyridazine-5,8-dione; sodium salt of 4-amino-7-(β-D-ribofuranosile)pyrimido[4,5-d]-6H-pyridazine-5,8-dione; sodium salt of 2-bromo-7-(β-D-ribofuranosile)pyrimido[4,5-d]-6H-pyridazine-5,8-dione; sodium salt of 4-hydroxy-7-(β-D-ribofuranosile)pyrimido[4,5-d]-6H-pyridazine-5,8-dione; sodium salt of 4-carboxy-7-(β-D-ribofuranosile)pyrimido [4,5-d]-6H-pyridazine-5,8-dione; lithium salt of pyrimido[4,5-d]-6H-pyridazine-5,8-dione; sodium salt of 2-amino-pyrimido[4,5-d]-6H-pyridazine-5,8-dione; and potassium salt of 4-bromo-pyrimido[4,5-d]-6H-pyridazine-5,8-dione.

3. The method as claimed in claim 1, wherein the active ingredient is used as a neuroprotector in a pharmaceutical composition for protection of a nervous system.

4. The method as claimed in claim 1, wherein the active ingredient is used in a pharmaceutical composition for improvement of cognitive function and normalization of psychophysiological status.

5. The method as claimed in claim 1, wherein the active ingredient is used in a pharmaceutical composition of anxiolytic and antidepressive action.

6. The method as claimed in claim 1, wherein the diseases are selected from the group consisting of: diseases caused by drug abuse; insomnia; sexual disorders; gastro-intestinal disorders; psychoses; affective disorders; personality disorders; psychiatric disorders of mood; schizophrenia and schizoaffective disorders; polydipsia; anxiety and associated diseases; obesity; bacterial infections of the central nervous system; disorders of learning; disorders of memory; neurodegenerative diseases; extrapyramidal side effects of neuroleptics; hypothalamic-pituitary effects; dystonia; dyskinesia; hyperkinesis; dementia; ischemia; and motion disorders.

7. The method as claimed in claim 6, wherein the neurodegenerative disease is a Parkinson's disease or a Alzheimer's disease.

8. The method as claimed in claim 6, wherein the sexual disorder is a sexual dysfunction.

9. The method as claimed in claim 6, wherein the psychoses is an inorganic psychoses.

10. The method as claimed in claim 6, wherein the psychiatric disorders of mood is a bipolar disorder, dysphoric mania, or depression.

* * * * *